United States Patent
Kim

(10) Patent No.: US 9,098,955 B2
(45) Date of Patent: Aug. 4, 2015

(54) SYSTEM AND METHOD FOR INDICATING FUEL EFFICIENCY OF FLEXIBLE FUEL VEHICLE

(71) Applicant: Hyundai Motor Company, Seoul (KR)

(72) Inventor: Seong Un Kim, Hwaseong-si (KR)

(73) Assignee: Hyundai Motor Company, Seoul (KR)

(*) Notice: Subject to any disclaimer, the term of this patent is extended or adjusted under 35 U.S.C. 154(b) by 56 days.

(21) Appl. No.: 13/971,550

(22) Filed: Aug. 20, 2013

(65) Prior Publication Data
US 2014/0142835 A1    May 22, 2014

(51) Int. Cl.
| | | |
|---|---|---|
| *G07C 5/00* | (2006.01) | |
| *G01N 33/28* | (2006.01) | |
| *G01N 9/36* | (2006.01) | |
| *G01N 9/00* | (2006.01) | |
| *B60W 10/00* | (2006.01) | |
| *B60K 35/00* | (2006.01) | |

(52) U.S. Cl.
CPC ............... *G07C 5/004* (2013.01); *B60K 35/00* (2013.01); *B60W 10/00* (2013.01); *G01N 9/00* (2013.01); *G01N 9/36* (2013.01); *G01N 33/2829* (2013.01); *G07C 5/00* (2013.01); *B60K 2350/1092* (2013.01); *B60W 2560/04* (2013.01)

(58) Field of Classification Search
CPC ...... G07C 5/004; G07C 5/00; G01N 33/2829; G01N 9/36; G01N 9/00; B60W 10/00; B60W 2560/04; B60K 35/00
USPC .......................................................... 701/123
See application file for complete search history.

(56) References Cited

U.S. PATENT DOCUMENTS

| | | | | |
|---|---|---|---|---|
| 5,014,011 | A * | 5/1991 | Colvin ......................... | 324/663 |
| 5,211,147 | A * | 5/1993 | Ward ....................... | 123/406.47 |
| 7,219,539 | B1 * | 5/2007 | Bauerle ...................... | 73/114.54 |
| 2004/0139736 | A1* | 7/2004 | Yoshizawa et al. ............ | 60/285 |
| 2005/0144834 | A1* | 7/2005 | Jimeson et al. ................ | 44/302 |
| 2006/0169035 | A1* | 8/2006 | Kunter ............................ | 73/149 |
| 2009/0107215 | A1* | 4/2009 | Wakabayashi et al. ...... | 73/30.04 |
| 2010/0024288 | A1* | 2/2010 | Jimeson et al. ................ | 44/452 |
| 2010/0077834 | A1* | 4/2010 | Daniels et al. ............... | 73/23.31 |

FOREIGN PATENT DOCUMENTS

| | | |
|---|---|---|
| JP | S61-94719 A | 5/1986 |
| JP | 2007-303395 A | 11/2007 |
| JP | 2010-127160 A | 6/2010 |
| KR | 10-1997-0044827 | 7/1997 |
| WO | 9110824 A1 | 7/1991 |

\* cited by examiner

*Primary Examiner* — Mary Cheung
*Assistant Examiner* — Frederick Brushaber
(74) *Attorney, Agent, or Firm* — Mintz Levin Cohn Ferris Glovsky and Popeo, P.C.; Peter F. Corless

(57) ABSTRACT

A method and a system for indicating a fuel efficiency in a vehicle is provided that includes a density sensor configured to measure the density of a fuel mixture stored in a fuel tank. In addition, a controller is configured to derive the mix ratio related to the fuel mixture via the density measured by the density sensor and change a reference value of a fuel calculation logic based on the mix ratio. In addition, the controller is configured to determine the fuel efficiency based on the changed reference value.

10 Claims, 2 Drawing Sheets

SYSTEM AND METHOD FOR INDICATING FUEL EFFICIENCY OF FLEXIBLE FUEL VEHICLE

CROSS-REFERENCE TO RELATED APPLICATION

This application claims under 35 U.S.C. §119(a) the benefit of Korean Patent Application No. 10-2012-0132141 filed on Nov. 21, 2012 the entire contents of which are incorporated herein by reference.

BACKGROUND (a) Technical Field

The present invention relates to system and method for indicating fuel efficiency of a flexible fuel vehicle which improve reliability of a fuel efficiency indication in a cluster and a calculation of an actual fuel efficiency by increasing accuracy of a actual fuel mix ration determination.

(b) Background Art

Since FFVs (Flexible Fuel Vehicle) use a mixture of gasoline and ethanol as the fuel, fuel efficiency varies depending on the contents of the fuel, thus causing an error in a fuel efficiency indication and a DTE (Distance To Empty) indication in a cluster. Since the fuel is different in fuel properties for each area, error occurs in indicating the actual vehicle fuel efficiency and cluster fuel efficiency. Specifically, as a vehicle travels, the engine control unit (ECU) may calculate the traveling fuel efficiency, but the content of the fuel may not be reflected, thus is may be difficult to indicate the accurate fuel efficiency value.

In particular, since there is a difference in content of water in the same fuel, depending on the areas, it may be necessary first to determine the mix ratio of fuel to more accurately calculate the fuel efficiency. In addition, since the information is output to a user via a cluster, it is important to reflect the information to the cluster indication information.

In the gasoline/diesel vehicles presently on the market, an engine control unit (ECU) transmits a FCO (fuel consumption signal) to a cluster through CAN communication based on the fuel efficiency calculated using the revolutions per minute (RPM) and the amount of intake air during traveling. In addition, the cluster calculates and indicates the cluster fuel efficiency based on the information. In other words, the cluster outputs an increased fuel efficiency at a reference value and reflects the fuel efficiency calculated during traveling.

In FFVs, there is a difference of 20% or more in fuel efficiency, depending on the content of ethanol fuel and it is difficult to reflect a difference in fuel efficiency according to the mix ratio of fuel generated when filling the fuel tank with fuel. Thus, it may be difficult to indicate an accurate fuel efficiency value and rely on the data. Furthermore, when fuel includes different mix ratios of fuel, it may be difficult to correct errors in the fuel efficiency output.

In one exemplary prior art, alcohol fuel in a fuel tank is injected from a secondary injection valve in a normal status, while gasoline in a fuel tank is injected from a primary injection valve in starting the engine, in a cold environment, or in a high intake stroke. Furthermore, when a difference between the actual air-fuel ratio and a target air-fuel ratio is above a set value in feedback control the air-fuel ratio of a gas mixture in a normal status, gasoline with high heat is injected at the amount of correction fuel in feedback control of the air-fuel ratio. Accordingly, the amount of correction fuel reduces compared to when alcohol fuel with low heat is used as correction fuel, thus, the amount of fuel sticking to the inner wall of an intake channel reduces and fuel is more quickly supplied to an operation chamber. Therefore, the following responsiveness in feedback control of air-fuel ratio is improved and the fuel efficiency may be improved.

However, even in the technology of the related art, the fuel efficiency is reflected after traveling for a predetermined time and not after the fuel has been filled, thus decreasing the initial reliability.

The description provided above as a related art of the present invention is just for helping understanding the background of the present invention and should not be construed as being included in the related art known by those skilled in the art.

In the related art, it was general to find out the mix ratio of the filled fuel and find out the fuel efficiency, by driving a vehicle for a predetermined time and leaning the result of the driving to find out the fuel efficiency.

However, according to such a method, since it was required to drive a vehicle for a predetermined time, it was difficult to guide accurate fuel efficiency, and accordingly, the fuel efficiency rapidly changes after a little time, so the consumers were confused and complained in some cases.

SUMMARY

The present invention provides a system and method for indicating fuel efficiency of a fuel flexible vehicle (FFV) which improve reliability in a fuel efficiency indication on a cluster and a calculation of an actual fuel efficiency by increasing the accuracy of an actual fuel mix ration determination.

Furthermore, the system for indicating the fuel efficiency in an FFV includes: a density sensor configured to measure the density of a fuel mixture stored in a fuel tank; and a fuel efficiency determining unit configured to derive the mix ratio related to the fuel mixture via the density measured by the density sensor, to change a reference value of a fuel calculation logic based on the mix ratio, and to determine the fuel efficiency based on the changed reference value.

The fuel efficiency determining unit may have a fuel data map composed of densities and mix ratios and may derive a mix ratio by inserting the density into the fuel data map. In addition, the fuel calculation logic of the fuel efficiency determining unit may derive the distance-to-empty according to the amount of the filled fuel as fuel efficiency, and when the reference value of the fuel efficiency calculation logic for calculating the distance-to-empty changes, the fuel efficiency determining unit may determine the distance-to-empty based on the changed reference value.

Furthermore, the fuel efficiency determining unit may derive the mix ratio of a fuel mixture from the density measured by the density sensor, when a fuel-filling mode of a vehicle is turned off, change a reference value of a fuel efficiency calculation logic based on the mix ratio, and determine fuel efficiency based on the changed reference value.

The system may further include a cluster configured to output the fuel efficiency determined by the fuel efficiency determining unit wherein the fuel efficiency determining unit may be disposed in the cluster.

Another system for indicating fuel efficiency of an FFV of the present invention includes: a density sensor configured to measure the density of a fuel mixture stored in a fuel tank; an engine control unit (ECU) configured to derive the mix ratio of the fuel mixture from the density measured by the density sensor; and a fuel efficiency determining unit configured to change a reference value of a fuel calculation logic based on the mix ratio derived by the ECU and determine the fuel efficiency based on the changed reference value.

A method of indicating a fuel efficiency of an FFV of the present invention includes: measuring the density of a fuel fixture stored in a fuel tank; deriving a mix ratio related to the fuel mixture via the density; changing a reference value of a fuel efficiency calculation logic based on the mix ratio; and determining fuel efficiency using the fuel efficiency calculation logic based on the changed reference value.

Furthermore, the deriving of the mix ratio via the density may include using a fuel data map composed of densities and mix ratios.

Additionally, the fuel efficiency determining unit may derive a distance-to-empty according to the amount of filled fuel as fuel efficiency, using the fuel efficiency calculation logic with a changed reference value. The determining fuel efficiency step may further include outputting the determined fuel efficiency to a cluster. Further, measuring the density may further include measuring the density of a fuel mixture stored in a fuel tank, when a fuel-filling mode of a vehicle is turned off.

Moreover, a method of indicating a fuel efficiency of an FFV may be include deriving a mix ratio related to a fuel mixture via a density of a fuel mixture stored in a fuel tank, changing a reference value of a fuel efficiency calculation logic based on the mix ratio, and determining fuel efficiency based on the changed reference value.

BRIEF DESCRIPTION OF THE DRAWINGS

The above and other features of the present invention will now be described in detail with reference to exemplary embodiments thereof illustrated the accompanying drawings which are given hereinbelow by way of illustration only, and thus are not limitative of the present invention, and wherein.

Figure 1:
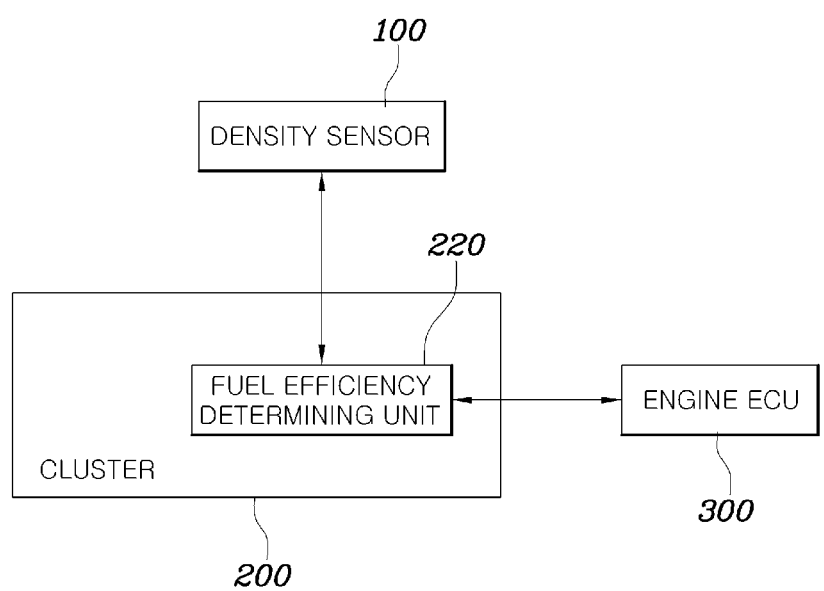
FIG. 1 is an exemplary diagram illustrating the configuration of a system for indicating fuel efficiency in a fuel flexible vehicle according to an exemplary embodiment of the present invention.

It should be understood that the accompanying drawings are not necessarily to scale, presenting a somewhat simplified representation of various exemplary features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Furthermore, the control logic of the present invention may be embodied as non-transitory computer readable media on a computer readable medium containing executable program instructions executed by a processor, controller or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

A system and method for indicating a fuel efficiency in a flex fuel vehicle (FFV) according to an exemplary embodiment of the present invention are described hereafter with reference to the accompanying drawings.

FIG. 1 is an exemplary diagram illustrating the configuration of a system for indicating fuel efficiency in an FFV vehicle according to an exemplary embodiment of the present invention. A system for indicating a fuel efficiency in an FFV of the present invention includes: a density sensor 100 configured to measure the density of a fuel mixture stored in a fuel tank; and a fuel efficiency determining unit 220, executed by a controller to derive the mix ratio of the fuel mixture from the density measured by the density sensor 100, change a reference value of a fuel calculation logic based on the mix ratio, and determine the fuel efficiency on the basis of the changed reference value.

The present invention relates to an FFV that uses a fuel mixture of ethanol and gasoline for traveling. Since two or more fuel types may be used in an FFV and the mixed fuels exhibit different properties, it may be difficult to distinguish the specific fuel types in the FFV. Therefore, fuel efficiency calculations may vary depending on the mix ratio. Thus, the present invention provides a system and method for calculating a substantially accurate fuel efficiency by determining the mix ratio of the two fuels and informing a vehicle driver of the fuel efficiency.

Moreover, the present invention provides a method of calculating a mix ratio from the density of the fuel. Furthermore, the system for indicating fuel efficiency in an FFV may include a density sensor 100 configured to measure the density of a fuel mixture stored in the fuel tank. In general, there is a difference in density between gasoline and ethanol used as fuel for an FFV. The densities of gasoline, ethanol, and water are about 0.66~0.75, 0.79, and 1.0, respectively. Therefore, a driver using an FFV may select the ratio of gasoline and ethanol thereby resulting in a density difference in the mixed fuel. Thus, since the density of filled fuel may be measured by a density sensor attached to a fuel tank, the mix ratio of fuel may be determined from the density.

Further, the fuel efficiency determining unit 220, operated by a controller, may be configured to derive a mix ratio of a fuel mixture from the density measured by the density sensor 100. Additionally, the reference value of the fuel efficiency calculation logic may be changed based on the mix ratio and the fuel efficiency may be determined based on the changed reference value.

In other words, the fuel efficiency determining unit 220 may use a fuel data map composed of density and mix ratios. Further, the mix ratio may be derived by inserting the measured density into the fuel data map. In this configuration, when fuel is filled with various mix ratios, the fuel efficiency may be calculated and the mix ratio of the fuel may be calculated after the fuel is filled.

Moreover, the fuel calculation logic of the fuel efficiency determining unit 220 may derive the distance-to-empty according to the amount of the filled fuel as the fuel efficiency, and when the reference value of the fuel efficiency calculation logic for calculating the distance-to-empty changes, the distance-to-empty may be determined based on the changed reference value.

In other words, the fuel efficiency includes the distance-to-empty of the vehicle, and reliability of the fuel efficiency may be improved by consistently informing the driver of the distance-to-empty, when traveling for a predetermined time, and by informing the driver of the distance-to-empty after filling the vehicle with the fuel. Furthermore, the distance-to-empty may be changed by a correction in traveling, but not beyond the correction through the traveling distance and the amount of consumed fuel transmitted from an ECU. On the contrary, the accuracy may be improved by calculating the distance-to-empty based on the mix ratio when fuel is filled, in comparison to calculating and guiding the distance-to-empty based on the properties of the fuel that has been filled, in calculating the distance-to-empty to indicate after filling.

According to the present invention, a fuel efficiency determination unit 220 may be controlled by a controller to derive the mix ratio of the fuel mixture from the density measured by the density sensor, when the filling mode of a vehicle is turned off, (e.g., when the engine starts after the fuel is filled, when a short time has passed after starting the engine, or a predetermined vehicle speed is reached) change the reference value of the fuel calculation logic based on the mix ratio, and determine the fuel efficiency based on the changed reference value. In other words, as a new mix ratio is determined and used after the fuel is filled, the reference value when fuel is filled at different mix ratios in the related art is not used, thus increasing the accuracy of an actual distance-to-empty calculation.

In particular, the fuel efficiency calculation logic of the fuel efficiency determining unit 220 may be categorized into post fuel filling phase and in traveling phase. In the post fuel filling phase, the mix ratio may be reflected and the reference value may be changed, and accordingly, an expected distance-to-empty may be calculated by multiplying the amount of the filled fuel by the changed reference value. For example, when the reference value according to the mix ratio of the related art is 12 per liter, the reference value according to a new mix ratio per liter changes to 13.

Meanwhile, in the in traveling phase, the actual distance-to-empty may be calculated by adjusting the fuel efficiency using the amount of air, the amount of consumed fuel, the traveling distance, and the RPM obtained from the ECU or other measurers.

Further, the present invention may further include a cluster 200, operated by the controller to output the fuel efficiency determined by the fuel efficiency determining unit 220. Additionally, the fuel efficiency determining unit 220 may be disposed in the cluster 200.

Another system for indicating fuel efficiency in an FFV of the present invention includes: a density sensor 100 configured to measure the density of a fuel mixture stored in a fuel tank; an ECU 300 configured to derive the mix ratio of the fuel mixture from the density measured by the density sensor; and a fuel efficiency determining unit 220, operated by a controller to change a reference value of a fuel calculation logic based on the mix ratio derived by the ECU and determine the fuel efficiency based on the changed reference value. In this configuration, the ECU may be configured to receive the density from the density value and calculate the mix ratio, and the distance-to-empty may be transmitted to the mix ratio to the fuel efficiency determination unit and to be calculated and output in the cluster.

However, the present invention is not limited thereto, the fuel efficiency determining unit 220 may be designed, for example, wherein the cluster 200 may be configured to determine the mix ratio and the ECU 300 may be configured to determine the fuel efficiency, or the cluster 200 may be configured to determine both the mix ratio and the fuel efficiency, or the ECU 300 may be configured to determine both the mix ratio and the fuel efficiency. Meanwhile, the present CAN communication system may be used together with the cluster, when determining the mix ratio and the fuel efficiency and the information may be transmitted to the ECU, in the various ways. Alternatively, when the ECU determines the mix ratio, the ECU may adjust the amount of consumed fuel based on the information and may transmit the adjusted amount of consumed fuel to the cluster, thereby increasing the accuracy of the distance-to-empty calculation.

Figure 2:
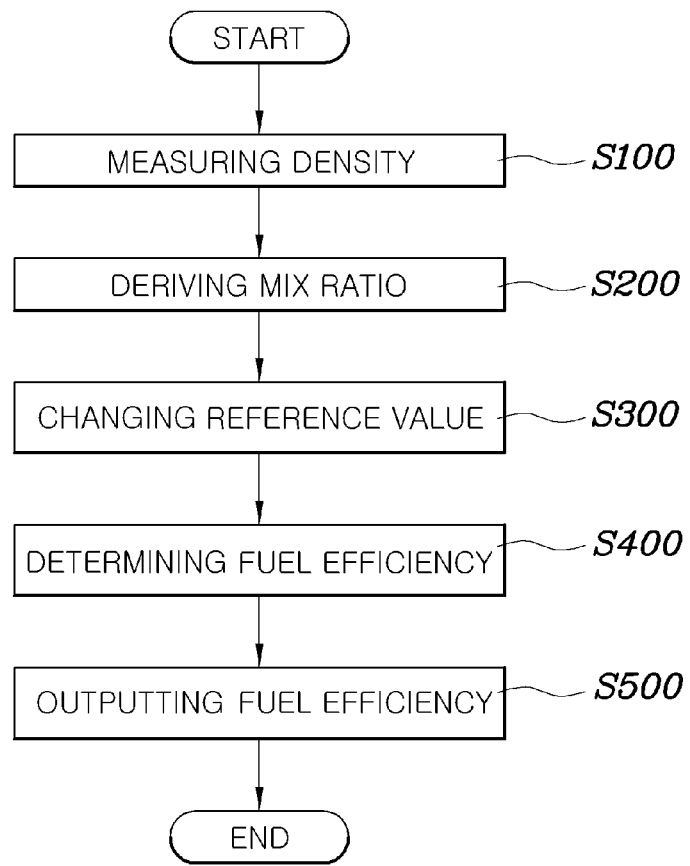
FIG. 2 is an exemplary flowchart illustrating a method of indicating fuel efficiency in a fuel flexible vehicle according to an exemplary embodiment of the present invention.

FIG. 2 is an exemplary flowchart illustrating a method of indicating a fuel efficiency of an FFV according to an exemplary embodiment of the present invention. The method of indicating fuel efficiency of an FFV may include: measuring, by a density sensor, the density of a fuel fixture stored in a fuel tank (S100); deriving, by a controller, a mix ratio of the fuel mixture from the density (S200); changing, by the controller, a reference value of a fuel efficiency calculation logic based on the mix ratio (S300); and determining, by the controller, the fuel efficiency using the fuel efficiency calculation logic based on the changed reference value (S400).

Further, deriving the mix ratio (S200) from the density, may include using a fuel data map composed of densities and mix ratios and the controller may derive a distance-to-empty according to the amount of filled fuel as the fuel efficiency, using the fuel efficiency calculation logic with a changed reference value, thus improving the reliability in deriving the distance-to-empty after filling the fuel.

Moreover, determining the fuel efficiency (S400) may further include outputting, by the controller, the determined fuel efficiency to the cluster (S500) and measuring density (S100) may allow a new fuel efficiency to be reflected after filling the fuel, by measuring the density of the fuel mixture stored in the fuel tank, when the fuel-filling mode of the vehicle is turned off.

The system and method for indicating a fuel efficiency of an FFV configured as described above, may reflect the difference in the fuel efficiency due to the mixed amount of fuel may increase the accuracy of the fuel efficiency value and the reliability of the data by reflecting the information when the fuel is filled. In addition, fuel efficiency may be improved by following the substantially accurate mixing amount of fuel of an FFV, using the information on the mixing amount of fuel in the ECU.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A system for indicating a fuel efficiency of a vehicle, comprising:
   a density sensor configured to measure a density of a fuel mixture stored in a fuel tank as being attached to a fuel tank; and
   a fuel efficiency determining unit configured to:
      derive a mix ratio by inserting the density measured by the density sensor into a fuel data map composed of densities and mix ratios;
      change a reference value of a fuel calculation logic based on the mix ratio; and
      determine the fuel efficiency based on the changed reference value, wherein the fuel efficiency determining unit is operated by a controller.

2. The system of claim 1, wherein the fuel calculation logic is configured to derive the distance-to-empty according to the amount of the filled fuel as the fuel efficiency, and when the reference value of the fuel efficiency calculation logic for calculating the distance-to-empty changes, the fuel calculation logic is configured to determine the distance-to-empty based on the changed reference value.

3. The system of claim 1, wherein the fuel efficiency determining unit is further configured to:
   derive the mix ratio related to the fuel mixture via the density measured by the density sensor, when a fuel-filling mode of the vehicle is turned off;
   change the reference value of the fuel efficiency calculation logic based on the mix ratio; and
   determine the fuel efficiency based on the changed reference value.

4. The system of claim 1, further comprising,
   a cluster configured to output the fuel efficiency that is determined by the fuel efficiency determining unit.

5. The system of claim 4, wherein the fuel efficiency determination unit is disposed in the cluster.

6. A method of indicating a fuel efficiency of an FFV, comprising:
   measuring, by a density sensor, a density of a fuel fixture stored in a fuel tank;
   deriving, by a fuel efficiency determining unit, a mix ratio using a fuel data map composed of densities and mix ratios;
   changing, by the fuel efficiency determining unit, a reference value of a fuel efficiency calculation logic based on the mix ratio; and
   determining, by the fuel efficiency determining unit, the fuel efficiency using the fuel efficiency calculation logic based on the changed reference value,
   wherein the fuel efficiency determining unit is controlled by a controller.

7. The method of claim 6, further comprising:
   deriving, by the fuel efficiency determining unit, a distance-to-empty according to the amount of filled fuel as the fuel efficiency, using the fuel efficiency calculation logic with a changed reference value.

8. The method of claim 6, wherein the determining fuel efficiency further includes:
   outputting, by the fuel efficiency determining unit, the fuel efficiency to a cluster.

9. The method of claim 6, wherein the measuring density includes measuring, by the fuel efficiency determining unit, the density of a fuel mixture stored in a fuel tank, when a fuel-filling mode of a vehicle is turned off.

10. A non-transitory computer readable medium containing program instructions executed by a processor or controller, the computer readable medium comprising:
    program instructions that control a density sensor to measure a density of a fuel fixture stored in a fuel tank;
    program instructions that control a fuel efficiency determining unit to derive a mix ratio using a fuel data map composed of densities and mix;
    program instructions that control the fuel efficiency determining unit to change a reference value of a fuel efficiency calculation logic based on the mix ratio; and
    program instructions that control the fuel efficiency determining unit to determine the fuel efficiency using the fuel efficiency calculation logic based on the changed reference value.

* * * * *